United States Patent

Soloman

[11] Patent Number: 5,363,968
[45] Date of Patent: Nov. 15, 1994

[54] AUTOMATIC BLISTER INSPECTION SYSTEM

[75] Inventor: Sabrie B. Soloman, Ridgewood, N.J.

[73] Assignee: Pfizer Inc., New York, N.Y.

[21] Appl. No.: 749,098

[22] Filed: Aug. 23, 1991

[51] Int. Cl.$^5$ .......................... B07C 5/00; G01B 11/00
[52] U.S. Cl. ..................... 209/546; 209/580; 209/587; 209/939; 348/92; 356/394; 250/223 R; 198/725
[58] Field of Search ............... 209/546, 576, 577, 580, 209/581, 587, 922, 934, 936, 939; 358/101, 106, 107; 356/237, 239, 394, 398; 250/223 B, 223 R; 198/341, 718, 725, 726

[56] References Cited

U.S. PATENT DOCUMENTS

| | | | |
|---|---|---|---|
| 4,118,730 | 10/1978 | Lemelson | 358/106 X |
| 4,354,602 | 10/1982 | Miyoshi et al. | 209/586 X |
| 4,414,566 | 11/1983 | Peyton et al. | 358/106 X |
| 4,488,648 | 12/1984 | Claypool | 209/526 |
| 4,582,201 | 4/1986 | Taniguchi et al. | 209/587 |
| 4,593,190 | 6/1986 | Kawasaki et al. | 209/522 X |
| 4,924,088 | 5/1990 | Carman et al. | 209/576 X |
| 4,980,292 | 12/1990 | Elbert et al. | 250/223 R X |
| 5,040,353 | 8/1991 | Evans et al. | 209/644 X |
| 5,065,237 | 11/1991 | Tsikos et al. | 358/101 |
| 5,091,963 | 2/1992 | Litt et al. | 358/101 X |
| 5,125,035 | 6/1992 | McCarthy et al. | 358/101 X |

FOREIGN PATENT DOCUMENTS

55-52811  4/1980  Japan ................... 209/546

*Primary Examiner*—D. Glenn Dayoan
*Assistant Examiner*—Tuan N. Nguyen
*Attorney, Agent, or Firm*—Peter C. Richardson; Paul H. Ginsburg; Grover F. Fuller, Jr.

[57] ABSTRACT

An automatic blister system includes an inspection station into which blisters are delivered in seriatim. After inspection the blisters are removed from the inspection station. A transport assembly conveys the blister through the inspection station. A sensor or detector is mounted in the inspection station directed at the path of travel of the blisters. In addition, a high speed camera is in the inspection station which is actuated by the sensor for capturing a picture of the blister. The characteristics of the blister in the picture are then monitored.

22 Claims, 6 Drawing Sheets

AUTOMATIC BLISTER INSPECTION SYSTEM

BACKGROUND OF THE INVENTION

In modern manufacturing systems particularly in pharmaceuticals various devices, such as tablets or capsules are packaged in blisters. In order to assure meeting the quality standards, it is necessary to provide some form of inspection. Where high speed automated manufacturing techniques are used there are great difficulties in the ability to perform reliable inspection of various desired characteristics of the tablet/capsule or blister. It would be desirable if some system could be provided capable of being used with such high speed manufacturing techniques wherein the high degree of reliability desired for the inspection could be achieved.

SUMMARY OF THE INVENTION

An object of this invention is to provide an automatic vision inspection system capable of fulfilling the above needs.

A further object of this invention is to provide such a system capable of measuring a wide variety of different characteristics of the packaged products such as tablets/capsules.

In accordance with this invention, an inspection station is provided into which blisters are delivered at high speed. A transport assembly moves the blisters through the inspection station to a discharge conveyor. A detector or sensor is mounted in the inspection station directed at the path of travel of the blisters. The detector actuates a high speed camera in the inspection station for capturing a picture of the blister. The picture is then monitored, using computer technology, to determine if the desired characteristics are achieved.

In a preferred practice of the invention the high speed camera is of the frame grabber type. Light means such as a strobe light is provided to work simultaneously with the camera. The monitor preferably includes a visual monitor having computer electronic windows. The monitor is capable of measuring such characteristics as the color, shape, dimensions, count, blister seal, surface flaws and product integrity.

DETAILED DESCRIPTION

FIGS. 1-4 show an automatic vision inspection system 10 for blisters in accordance with this invention. As shown therein the system 10 is designed to deliver error-free blisters by the use of vision inspection technology. System 10 is designed to be capable for delivering, for example, three blisters per second which enables the tablets/capsules contained in any blister to be measured for defects in, for example, shape, size, flaws, or micro deformity.

As shown therein, system 10 includes an upstream feed section 12 which feeds individual blisters 14 into an inspection station 16. The inspection station includes a detector or sensor 18 which actuates a camera 20 to capture a picture of the blister. A monitor assembly 22 including monitor screen 24 is also located in inspection station 16 to visually indicate characteristics of the blister and the tablets/capsules therein which are being inspected. From the inspection station 16 the blisters are transported to a downstream discharge section 26. A transport assembly 28 is used to receive the blisters 14 from the discharge section 12, transport the blisters to inspection station 16 and discharge the blisters to discharge section 26.

Any suitable means may be used for conveying the blisters to inspection station 16. In the illustrated embodiment an endless belt or conveyor 30 is mounted around rollers 32 with the blisters 14 being conveyed on the upper run of conveyor belt 30.

Figure 3:
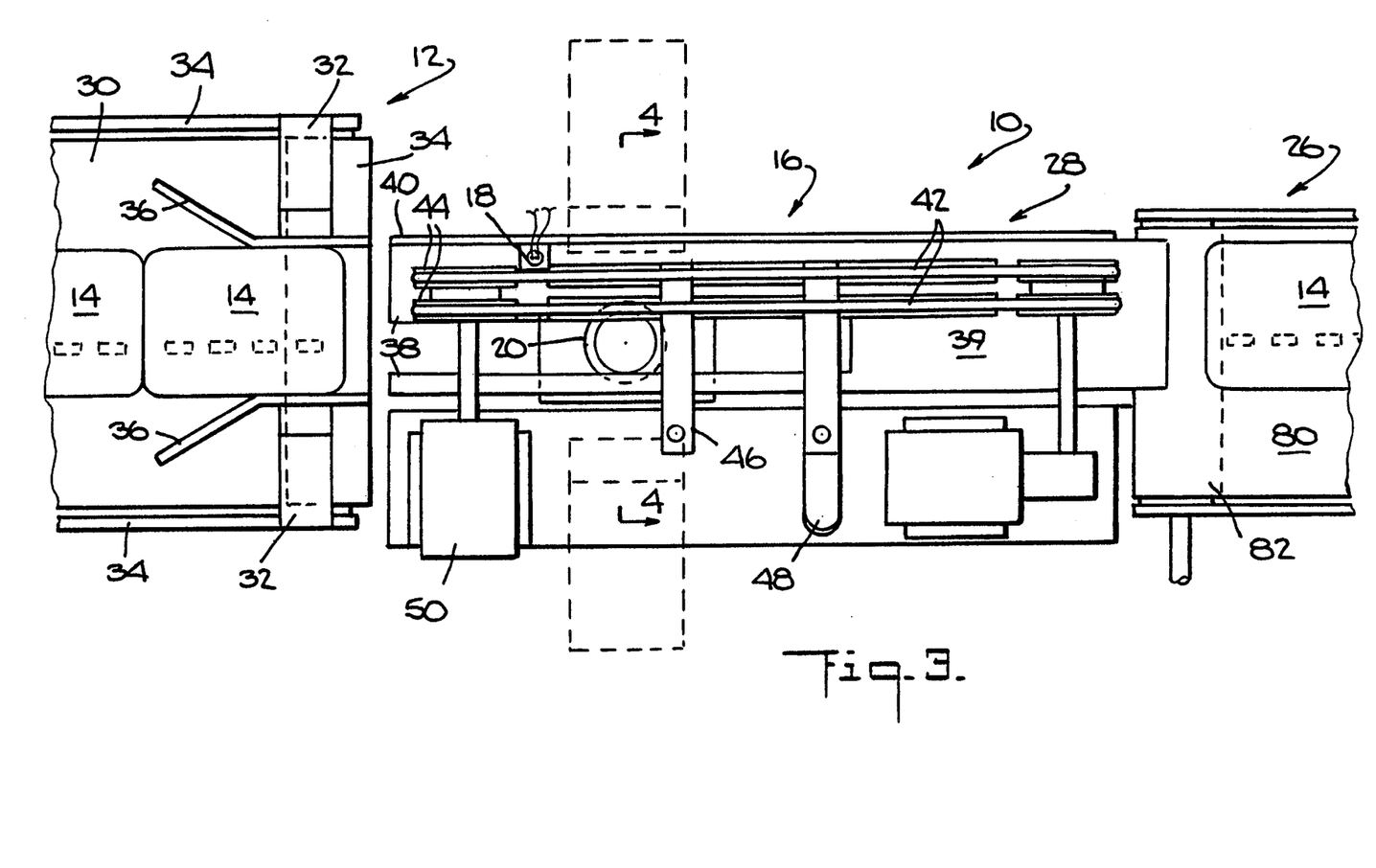
FIG. 3 is a top plan view of the system shown in FIGS. 1-2.

FIG. 3 illustrates the rollers 32 to be mounted on frame 34. As also shown therein a pair of guide plates 36 are disposed at the discharge end of feed section 12 to assure the proper alignment of blisters 14 on transport system 28.

Figure 2:
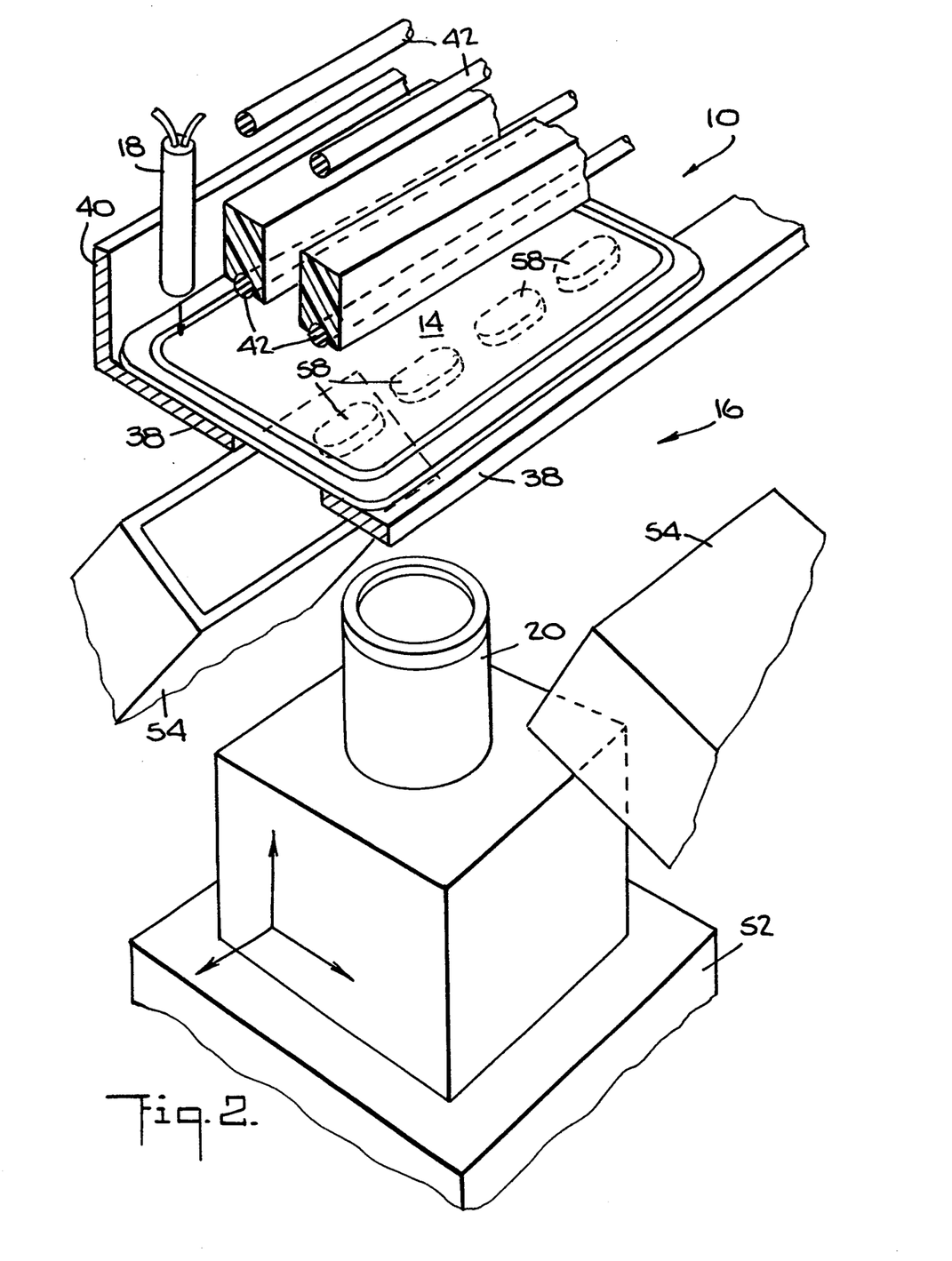
FIG. 2 is a perspective view partly in section of the system shown in FIG. 1.
Figure 4:
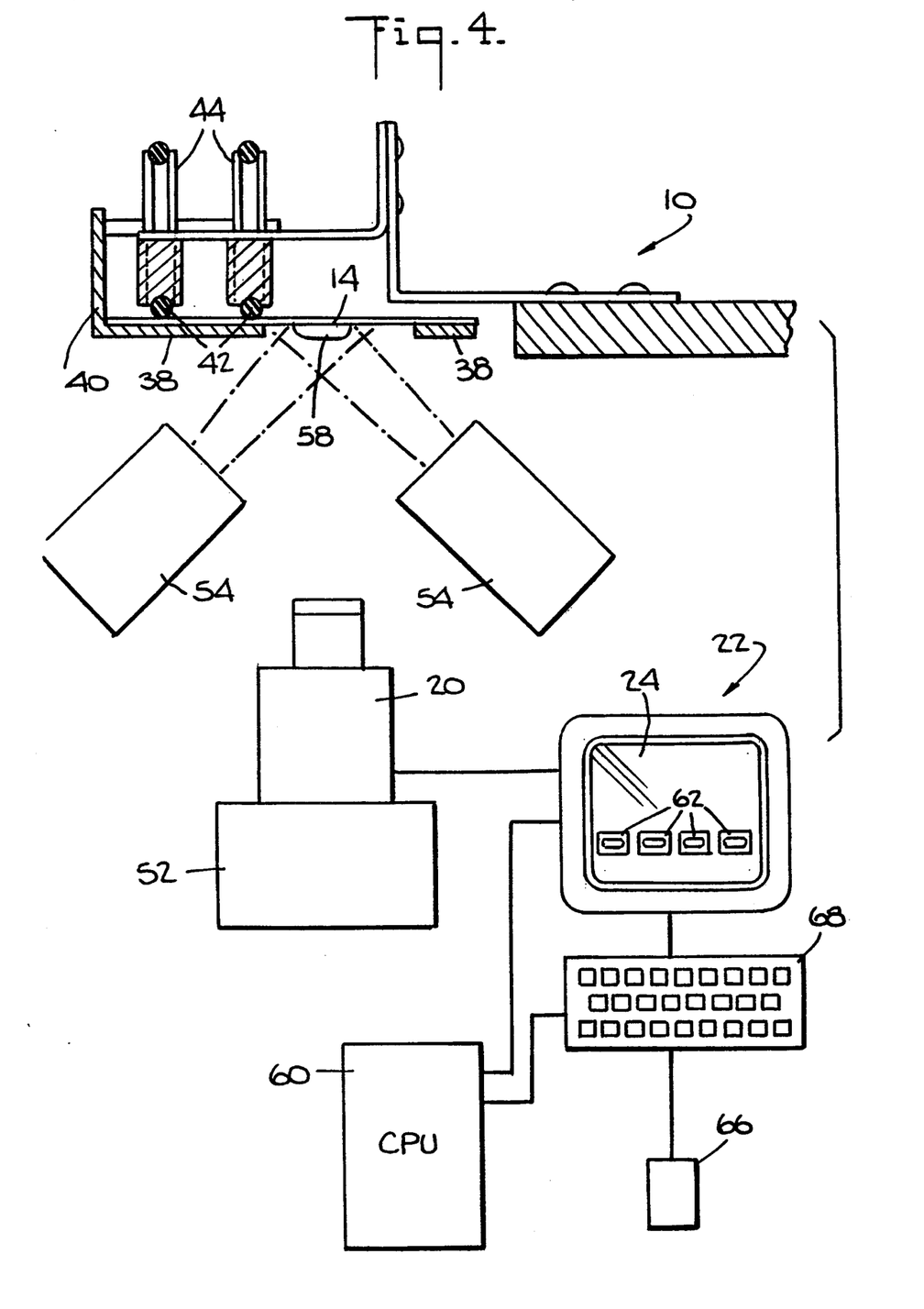
FIG. 4 is a cross-sectional view taken through FIG. 3 along the line 4—4.

As illustrated in FIGS. 2-4, transport system 28 includes a pair of spaced, parallel rails 38 which may include an upstanding guide flange 40. Rails 38 are disposed in line with conveyor belt 30 so that the rotating conveyor belt feeds each blister onto rails 38. Rails 38 may be extensions or cutouts from downstream platform 39. Mounted above rails 38 is a drive mechanism which includes a drive belt 42 mounted around rollers 44 and disposed above rails 38 a distance generally equal to the thickness of the blister pack so that the rotating drive belt 42 will contact the upper surface of the blister pack and frictionally drive the blister pack in a downstream direction away from feed section 12 toward discharge station 26. Preferably, rails 38 have a smooth or low friction upper surface to facilitate the sliding movement of the blister packs on the rails 38 while belt 42 is made of a higher friction material so that the drive belt 42 will not slip when urging the blister packs through the inspection station 16.

Figure 1:
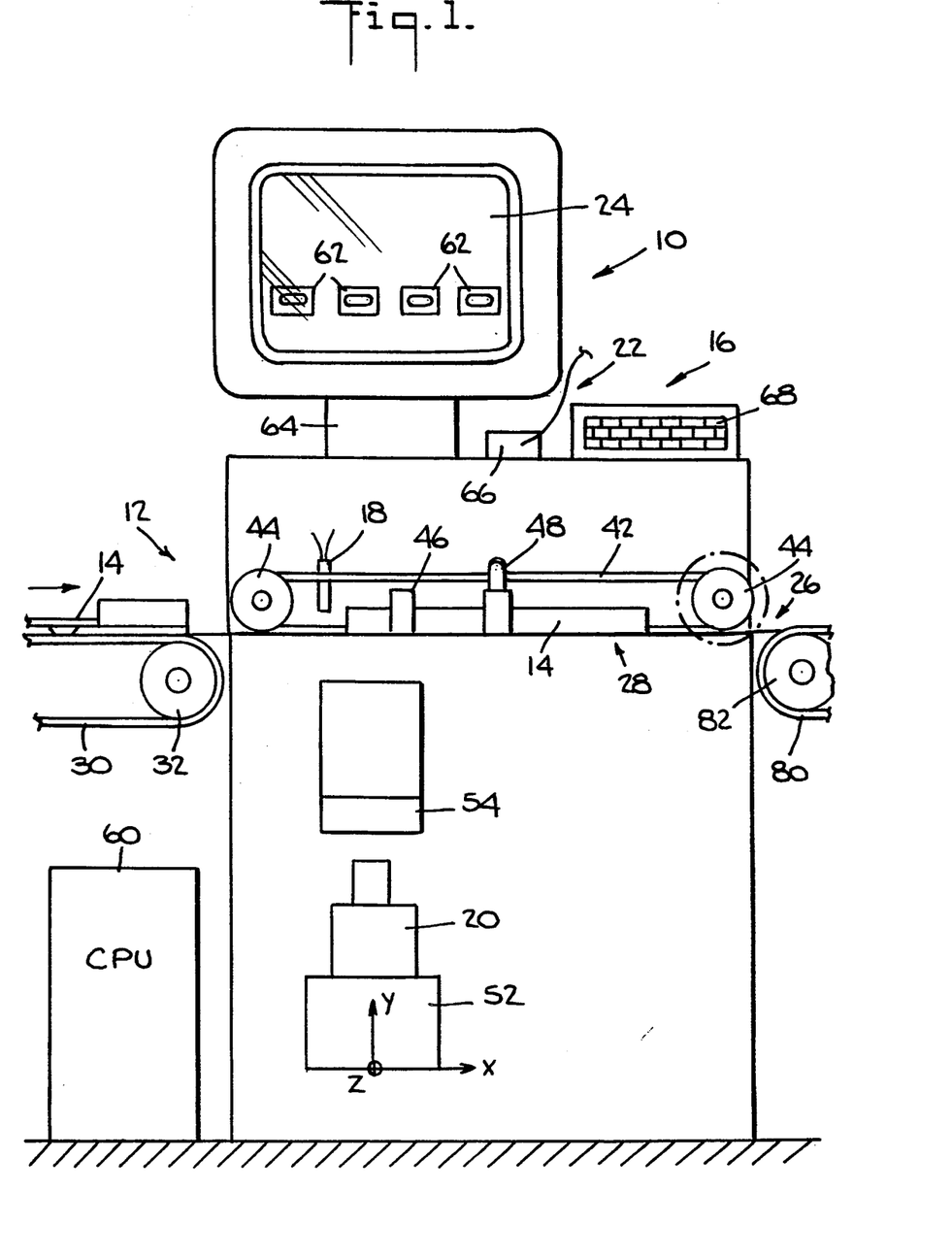
FIG. 1 is a side elevational view of an automatic blister inspection system in accordance with this invention.

As best shown in FIG. 1 the transport system 28 includes a latch 46 which may be inactivated to permit the entire unit to be raised and removed from inspection station 16. The raising of the unit is facilitated by the provision of an arm 48.

As most clearly shown in FIG. 2 rails 38 are spaced apart by a distance sufficient to permit the blisters 14 to be disposed in the gap between the rails without any visual obstruction from the view of camera 20. After passing the field of view of camera 20, the blisters are conveyed on platform 39 to discharge section 26.

It is to be understood that any suitable means may be used for conveying the blisters through the inspection station. In the illustrated embodiment, for example, a drive belt 42 is used to frictionally engage the blister pack and urge it in a downstream direction. Drive belt 42 is driven by rollers 44,44 with one of the rollers in turn being driven by a motor 50. Rails 38 may extend the length of station 16 without any platform or apron 39. Rails 38 may also be movable toward and away from each other to vary their spacing. What is important is that the blisters be conveyed in a reliable high speed manner with the individual blisters exposed to the camera 20 as the blisters move through inspection system 16. Additionally, the blisters must be in the line of view of sensor 18. Sensor 18 is operatively connected to camera 20 in any suitable manner to, for example, actuate camera 20 when the trailing edge of each blister pack is detected. If desired any other portion of the blister pack may be utilized to trigger the sensor. It is preferred, however, to use the trailing edge, since the trailing edge would also provide a line of reference or origin line which is used as later described to precisely locate any defects.

In order to facilitate the operation of camera 20, camera 20 is mounted on a support or table 52 capable in any suitable manner of three dimensional movement in the X, Y and Z directions as indicated, for example, in FIGS. 1 and 2 by the arrows. Accordingly, camera 20 may be precisely positioned at the desired location required by the specific blisters being conveyed through inspection station 20.

Figure 10:
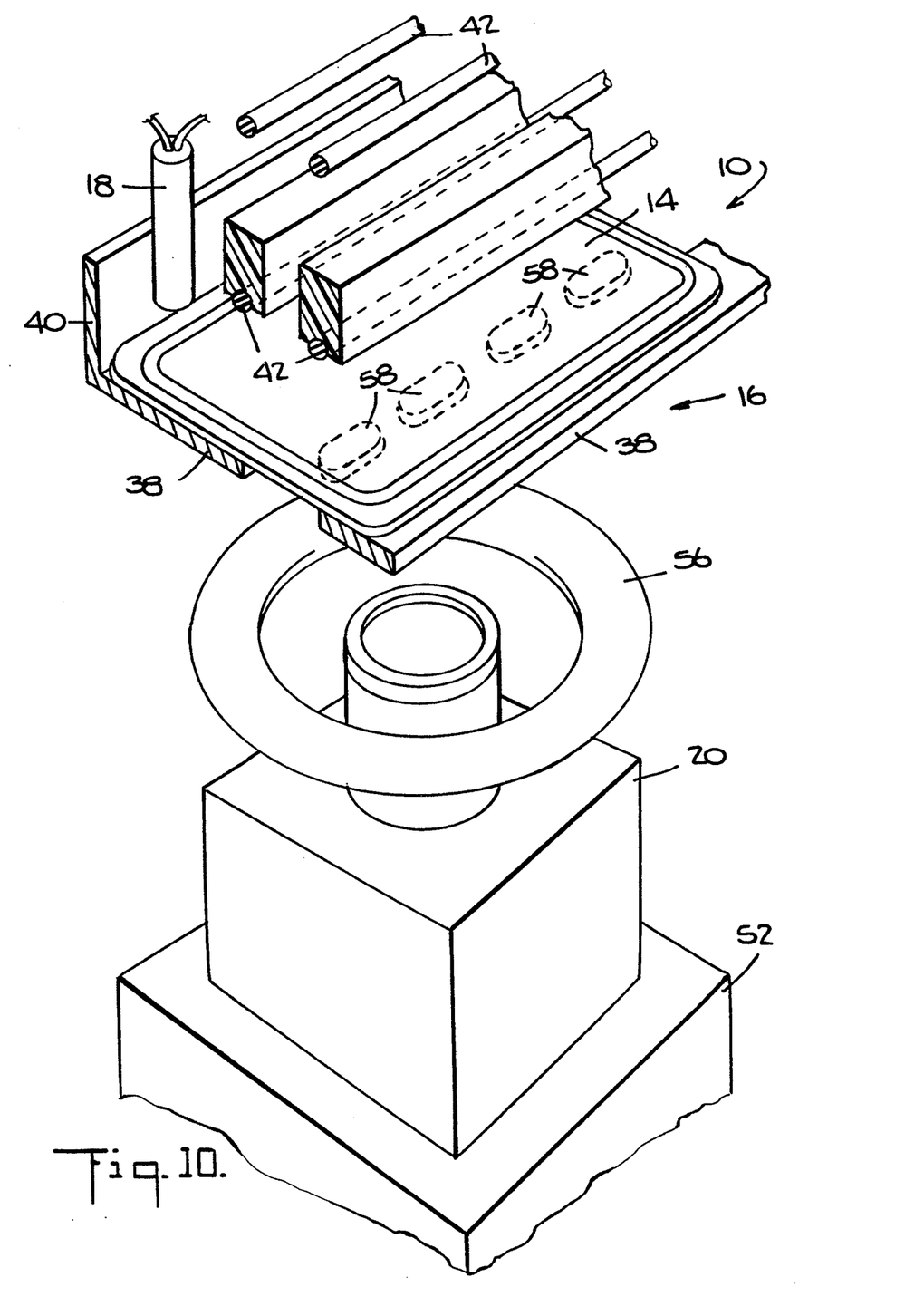
FIG. 10 is a perspective view similar to FIG. 2 of a modified form of system in accordance with this invention.

In the preferred practice of the invention, sensor 18 also actuates strobe lights simultaneously with the actuation of camera 20 to assure proper background lighting for the taking of a picture of each blister. FIGS. 1 and 2, for example, illustrate a pair of strobe lights 54 mounted in housings on each side of camera 20. FIG. 10 illustrates an alternative arrangement wherein a circular strobe light 56 is utilized.

Any suitable high speed camera system may be used for practicing the invention. In the preferred practice of the invention camera 20 applies the frame grabber technique simultaneously with the strobe lights to instantaneously seize the image of the desired product for inspection as the product passes through the field of view. When the actual detailed picture is being captured by the frame grabber system 20 various quantitative and qualitative means are computed by monitor system 22 to determine the acceptance level of the tablets/capsules 58 within each blister 14. Various known vision techniques, such as gray scale processes, binary processes, rulers measuring processes, maximum and minimum radii processes, window processes and blob processes are applied for example, to analyze correct color, shape, dimensions, accurate counts, blister seals, surface flaws, and product integrity. The invention may be utilized to identify and segregate product defects including missing tablets/capsules, crushed or broken tablets/capsules, foreign products (e.g. tablets/capsules other than the product scheduled to be running) misaligned blisters (e.g. blisters that are not cut properly), and unsealed blisters. Once the vision system has reached a decision concerning each blister at hand, the system has the ability to automatically reject the defective blister or to stop the entire production line. In addition, an on/off button may be utilized on the control panel to give the operator the option of manually stopping the entire system.

As noted above, the invention may be practiced by incorporating means to automatically reject the defective blister. This may be accomplished by any suitable means. In the preferred practice a piston is located perpendicular to the path of travel of the blisters on discharge conveyor 80. The extension/retraction of the piston would be controlled by a further sensor also directed toward the path of travel of the blister. The computer would alert the sensor of the location in the line of a defective blister. When the sensor detects the leading edge of the defective blister, the sensor would actuate the piston to extend the piston into contact with the defective blister to eject the blister from the line and into a collecting bin.

The invention is thus capable of performing all the necessary vision computation on all products contained in any blister form. Various computer electronic windows are utilized to direct the inspection operation to specific type of products without any possible error in the selection process.

Any suitable computer means may be utilized to monitor and analyze the product being inspected. FIG. 1, for example, illustrates the monitor system to include a CPU 60 which may be located at any suitable area including an area completely remote from the remainder of inspection station 16. CPU 60 would store reference data for comparison purposes to determine when defects are present. The monitor system also includes a monitor screen 24 which is shown as having a plurality of computer electronic windows 62 on monitor screen 24. In the illustrated embodiment of FIG. 1 the monitor is mounted on a neck 64. Additionally, the system includes a suitable mouse 66 and keyboard 68. The on/off button for manually stopping the production system may be located at any suitable location including being part of or near keyboard 68. The windows 62 would visually show the tablets or capsules 58 in each blister.

Figure 5:
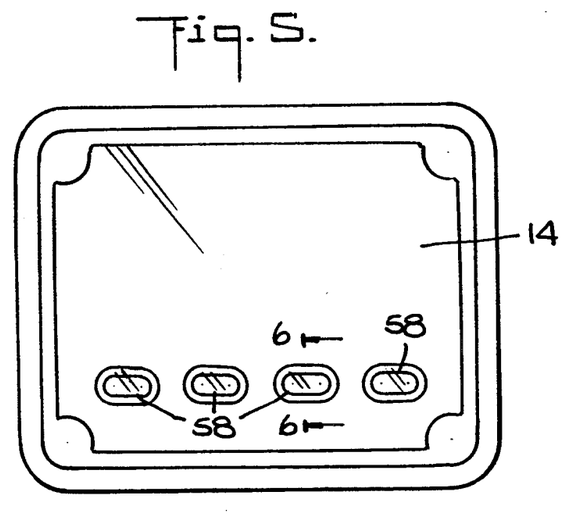
FIG. 5 is a top plan view of a blister which would be inspected by the system of FIGS. 1-4.
Figure 6:
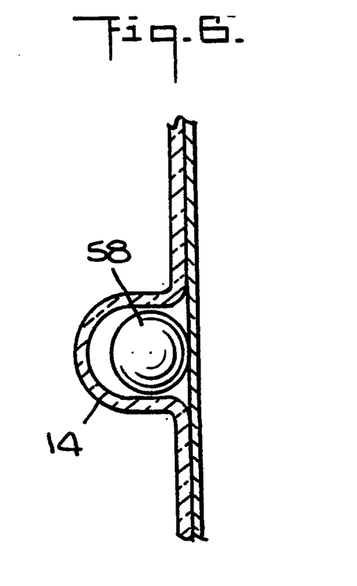
FIG. 6 is a cross-sectional view taken through FIG. 5 along the line 6—6.
Figure 7:
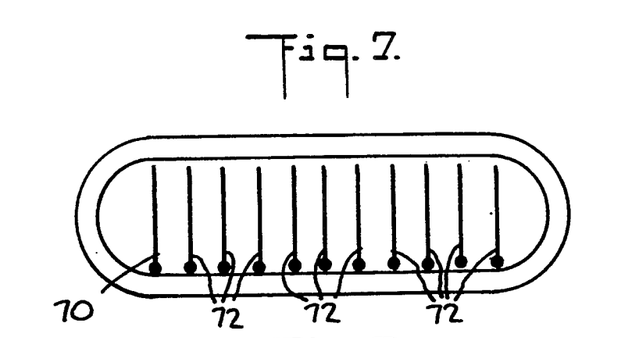
FIGS. 7-9 are front elevational views of computer electronic windows for monitoring a blister in the system of FIGS. 1-4.
Figure 8:
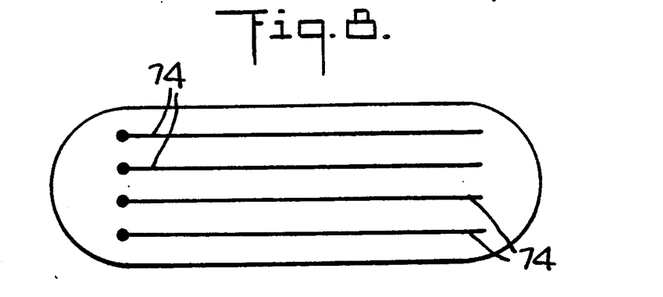
Figure 9:
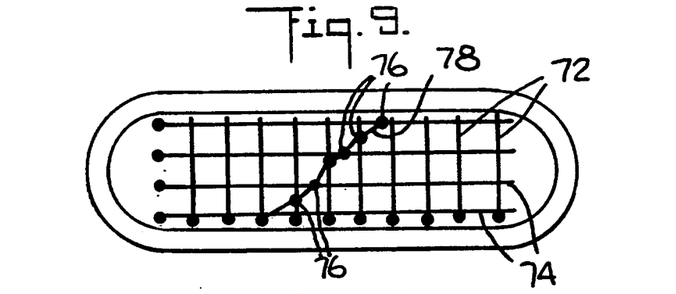

FIGS. 5–6 illustrate a blister 14 having a plurality of individual separated capsules or tablets 58 therein. In operation detector or sensor 18 would view the path of travel of the blisters between spaced rails 38. When a blister 14 is detected by sensor 18 the system waits until the blister has passed completely and the trailing edge is detected before a picture is taken by camera 20. After a picture has been taken a window is drawn at the left of the blister to find the blister edge. If no edge is detected then the system indicates an error message that the blister is not found. If the edge is found then an origin mark 70 (FIG. 7) is drawn on the edge of the blister in the middle of the screen 24 vertically. All subsequent measurements are done relative to the blister origin. Using the stored data in CPU 60, regarding the first product location in the top row, horizontal and vertical rulers are drawn in an attempt to detect how much difference there is in the nominal product position, relative to the origin versus the actual production position. Because of possible false edges being detected with this method the ruler distances need not be within a specified tolerance in order to allow the adjustment of the product location to occur. FIG. 7, for example, illustrates a series of vertical lines 72 in addition to origin line 70. FIG. 8 illustrates a plurality of horizontal lines 74 which in conjunction with vertical lines 70,72 would form a grid, such as shown in FIG. 9. If, for example, there is a crack in the tablet 58 being analyzed the screen will indicate the crack by a series of dots 76 along the appropriate vertical and horizontal grid lines. When connected the dots illustrate the precise location and extent of the crack 78.

During operation sheets of pictures of the capsules will be analyzed by system 10. The system may be utilized for example for products containing two tablets/capsules, four tablets/capsules or ten tablets/capsules. After the system is running and a blister has been analyzed the color indicator, such as green, will indicate that the product has passed all tests. A different color, such as red, will indicate that a defective product has been detected. Upon detecting a defective product binary 1/0 signals will be sent to the system to either sound an alarm and/or energize an eject mechanism and/or stop the production line. The information as to why the error has occurred will be displayed in the monitor window 24. If desired, a predetermined number of pictures can be saved in a memory bank to be recalled for analyzing the area. When the user-specified time period has been finished then the alarm will stop and the eject mechanism and line signals will be disabled. At this point, the vision system will be active and wait for the next blister.

Typically, the following tests may be run:

1. Standard deviation TEST

This test measures the consistency of the product. A window is drawn so that the product is enclosed in the window and the consistency is measured. If the product is not there or not whole, then this test should yield an error by generating a value that is too high.

2. Grayscale 1 TEST

This test checks for the correct color of the product. A window is drawn within the product and the average grayscale value is compared to the nominal grayscale values for the current product. If the measured value is too high or too low, then an error occurs.

3. Grayscale 2 TEST

This test is similar to the Grayscale 1 TEST. This allows for obtaining 2 grayscale readings in order to check for multi-colored capsules.

4. Background TEST

This test does a grayscale-type of test on the blister's background to determine if the blister was not sealed correctly.

5. Gray 1-2 TEST

This test checks the difference between the two grayscale readings.

6. Back-gray 1 TEST

This test checks the difference between the background reading and the grayscale 1 reading.

7. Back-gray 2 TEST

This test checks the difference between the background reading and the grayscale 2 reading.

8. Horizontal Radius TEST

This test checks the horizontal radius by drawing two rulers out from the product center and making sure that their sum lies within the minimum and maximum values.

9. Vertical Radius TEST

This test checks the vertical radius by drawing two rulers out from the product center and making sure that their sum lies within the minimum and maximum values.

10. Horizontal Broken TEST

This test checks for broken tablets by drawing a number of horizontal lines inside the product and checking if a specified number of those rulers detect edges.

11. Vertical Broken TEST

This test checks for broken tablets by drawing a number of vertical lines inside the product and checking if a specific number of those rulers detect edges.

12. Binary pixels TEST

This test checks the number of colored pixels detected within a specified window versus some calculated minimum and maximum values. If the product shows up as black pixels in the binary frame, then a smaller reading here means a bigger product.

As indicated, system 10 can be utilized for inspecting various types of different products. After a product is selected the system will display the "system running" in the status window and change its background color. Sheets passing through the system will then be checked for correctness. Various tests, which may be run are coded into the system. A screen initially shows a list of all possible tests. After one of the tests is selected, the parameters concerning that particular test would be shown. The first parameter is whether the test is enabled (non-zero) or disabled (0). The remaining parameters would deal, for example, with window sizes, ruler length, edge strength, etc. depending on the type of test.

After each blister 14 has passed through inspection station 16 it is conveyed by drive belt 42 to discharge section 26. Discharge section 26 may taken any suitable form, such as including a conveyor belt 80 mounted on rollers 82 to convey the blisters for further processing such as packaging.

As can be appreciated, the present invention thus utilizes known high speed camera techniques and computer technology to quickly analyze individual products in a high speed automated system and thereby assure that the quality standards required for the products are maintained. While the invention has been described with particular reference to the analyzing of tablets or capsules in blisters, for example, for pharmaceutical usage the invention may be practiced for inspecting any type of product in a high speed automation system.

What is claimed is:

1. An automatic vision blister inspection system for inspecting a blister and product included within the blister comprising an inspection station; a delivery conveyor for delivering blisters seriatim to said inspection station; a discharge conveyor for removing the blisters away from said inspection station; transport means for transporting the blisters though said inspection station from said delivery conveyor to said discharge conveyor, said transport means comprising a pair of spaced rails for supporting each monitored blister; a sensor in said inspection station directed at the path of travel of the blister on said transport means for detecting the moving blister; a high speed camera system in said inspection station activated by said sensor for capturing a picture of the blister, said high speed camera comprising a frame grabber camera, and said high speed camera being mounted on a support capable of moving in the X and Y and Z directions; and monitor means for monitoring the characteristics of the blister in said picture, said monitor means including computer means for determining quantitative and qualitative characteristics of the blister by analyzing said picture of the blister captured by said high speed camera system and comparing said quantitative and qualitative characteristics to nominal quantitative and qualitative characteristics for the blister.

2. The system of claim 1 wherein light means are provided in said inspection station, and said light means being actuated by said sensor.

3. The system of claim 2 wherein said light means comprises strobe light means.

4. The system of claim 3 wherein said strobe light means comprises a strobe light mounted in a housing on each side of said camera system.

5. The system of claim 3 wherein said strobe light means comprises a circular strobe light mounted around said camera system.

6. The system of claim 1 in combination with blisters having tablets/capsules therein.

7. The system of claim 1 wherein said sensor actuates said camera and said light means upon detection of an edge of said blister.

8. The system of claim 7 wherein said edge is the trailing edge.

9. The system of claim 1 wherein said transport means further comprises drive means disposed above said rails for urging the blister along said rails in a downstream direction.

10. The system of claim 9 wherein said drive means includes a drive belt for frictionally driving the blister.

11. The system of claim 10 wherein said sensor is disposed above said rails with its path of view directed toward the space between said rails, said camera being mounted below said rails directed toward said space between said rails whereby a blister containing a product may be disposed in said space between said rails to be sensed by said sensor and photographed by said camera, and said transport means being movably mounted to be removed from said inspection station.

12. The system of claim 10 wherein said monitor means includes a monitor screen for providing a visual inspection.

13. The system of claim 1 in combination with a plurality of blisters having tablets or capsules therein.

14. The system of claim 13 wherein said monitor includes computer means for determining the quantitative and qualitative characteristics of the blister such that said computer means utilizes vision technology including gray scale processes, binary processes, rulers measuring processes, maximum and minimum radii processes, window processes, and blob processes for analyzing the correct color, shape, dimensions, accurate count, blister seal, surface flaws, and product integrity of said tablets/capsules.

15. The system of claim 14 wherein said computer means includes computer electronic windows.

16. The system of claim 15 wherein said computer means operates by analyzing a grid characteristic of the product with said grid being formed by a horizontal and vertical lines and with dots being formed on said grid lines to indicate any break location in the product.

17. The system of claim 14 including means to reject defective blisters or products and means for stopping the production lines.

18. The system of claim 1 wherein said high speed camera system includes a frame grabber camera.

19. The system of claim 18 wherein said camera is mounted for movement in the X and Y and Z directions.

20. The system of claim 1 wherein said monitor means includes a monitor screen for permitting a visual inspection.

21. The system of claim 20 wherein said monitor means includes computer means for determining the quantitative and qualitative characteristics of the product being inspected.

22. A method of visually inspecting products packaged in blisters including the steps of conveying the blisters into an inspection station using a pair of spaced rails for supporting each blister and drive means disposed above said rails for urging the blister along said rails in a downstream direction; sensing the presence of the blisters in the sensing station; actuating a frame grabber camera in response to the sensing of the blister to capture a picture of the blister, said frame grabber camera being mounted on a support capable of moving in the X and Y and Z directions; monitoring the characteristics of the blister in the picture for determining the quantitative and qualitative characteristics of the blister by analyzing said picture; and comparing said quantitative and qualitative characteristics to nominal quantitative and qualitative characteristics for the blister.

* * * * *